US007726317B1

(12) United States Patent
Garcia

(10) Patent No.: US 7,726,317 B1
(45) Date of Patent: Jun. 1, 2010

(54) APPARATUS TO PROTECT A PIERCING

(76) Inventor: Yvonne Garcia, 18200 SW. 160 Ave., Miami, FL (US) 33187

( * ) Notice: Subject to any disclaimer, the term of this patent is extended or adjusted under 35 U.S.C. 154(b) by 204 days.

(21) Appl. No.: 11/865,782

(22) Filed: Oct. 2, 2007

(51) Int. Cl.
- *A61B 17/00* (2006.01)
- *A61F 13/00* (2006.01)
- *A61F 15/00* (2006.01)

(52) U.S. Cl. .................. 128/887; 128/888; 128/889; 602/42

(58) Field of Classification Search .......... 128/887, 128/888, 889; 602/42
See application file for complete search history.

(56) References Cited

U.S. PATENT DOCUMENTS

| 2,085,296 | A | * | 6/1937 | Carey | 5/630 |
| 4,667,666 | A | * | 5/1987 | Fryslie | 128/888 |
| 4,709,695 | A | * | 12/1987 | Kohn et al. | 128/858 |
| 4,969,881 | A | * | 11/1990 | Viesturs | 604/305 |
| 5,060,662 | A | * | 10/1991 | Farnswoth, III | 128/888 |
| 5,086,763 | A | * | 2/1992 | Hathman | 602/42 |
| 5,964,721 | A | * | 10/1999 | Augustine | 602/2 |
| 7,265,256 | B2 | * | 9/2007 | Artenstein | 602/42 |
| 7,487,779 | B2 | * | 2/2009 | Kurz et al. | 128/889 |
| 2003/0009122 | A1 | * | 1/2003 | Veras | 602/42 |
| 2006/0111656 | A1 | * | 5/2006 | Broyles | 602/42 |

* cited by examiner

*Primary Examiner*—Patricia M Bianco
*Assistant Examiner*—Victoria Hicks
(74) *Attorney, Agent, or Firm*—Albert Bordas, P.A.

(57) ABSTRACT

An apparatus to protect a body and facial piercing and its affected area during a healing period, has a body assembly. The body assembly has top and bottom faces, an exterior wall, and an interior wall. The body assembly further defines a cavity that extends inwardly from the interior wall. A permeable cover covers the top face and the cavity to allow ambient-air to enter and circulate therethrough. This allows healing of a body or facial piercing, and specifically the opening created by the piercing, and the surrounding area around the piercing. A removable cover covers the bottom face and the cavity. The bottom face has an adhesive, and the removable cover is removably attached to the bottom face.

10 Claims, 3 Drawing Sheets

APPARATUS TO PROTECT A PIERCING

BACKGROUND OF THE INVENTION

1. Field of the Invention

The present invention relates to body and facial piercing aftercare, and more particularly, to an apparatus to protect a piercing.

2. Description of the Related Art

Body and facial piercing usually refers to the piercing of a part of the human body for the purpose of wearing jewelry in an opening created. Body and facial piercing is an invasive procedure and is not without risks. These risks can be minimized in order to enjoy a safe and healthy piercing experience. Usually, a new piercing will be sore, tender or red for several days up to three weeks. Complete healing normally takes several weeks or more. During the healing period, care must be taken to avoid infection and touching is usually discouraged. Among the risks associated with body and facial piercing are bacterial and viral infections, particularly from contact or spilling with dirt and/or contaminated substances; and trauma, usually associated with unintended entanglement of the piercing jewelry with another object.

SUMMARY OF THE INVENTION

An apparatus to protect a piercing, comprising a body assembly. The body assembly comprises first and second faces, an exterior wall, and an interior wall. The body assembly further defines a cavity that extends inwardly from the interior wall. The body assembly is made out of a soft resilient material such as foam or sponge.

The instant invention also comprises a permeable cover that has a first cooperative shape and dimension to cover the top face and the cavity. The permeable cover is fixedly secured to the top face, whereby the top face has a first adhesive to keep the permeable cover fixedly secured thereon. The permeable cover covers the cavity to allow ambient-air to enter and circulate therethrough. This allows healing of a body or facial piercing, and specifically the opening created by the piercing, and the surrounding area around the piercing.

The instant invention also comprises a removable cover that has a second cooperative shape and dimension to cover the bottom face and the cavity. The bottom face has a second adhesive, and the removable cover is removably attached to the bottom face. The removable cover prevents foreign matter from accumulating within the cavity while the removable cover remains attached to the bottom face. The removable cover has a tab member.

The cavity is of a third cooperative shape and dimension to house the body or facial piercing. In the preferred embodiment, the body assembly is circular, oval, square, pentagonal, or hexagonal in shape, and the first face is parallel to the second face, and furthermore, the exterior wall is an exact shape as the interior wall.

It is therefore one of the main objects of the present invention to provide an apparatus to protect a body and facial piercing and its affected area during a healing period.

It is another object of the present invention to provide an apparatus to protect a piercing to avoid contact with unwanted objects and/or substances.

It is another object of the present invention to provide an apparatus to protect a piercing to prevent and/or reduce bacterial and viral infections.

It is another object of the present invention to provide an apparatus to protect a piercing to prevent and/or reduce trauma, usually associated with unintended entanglement of the piercing jewelry with another object.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
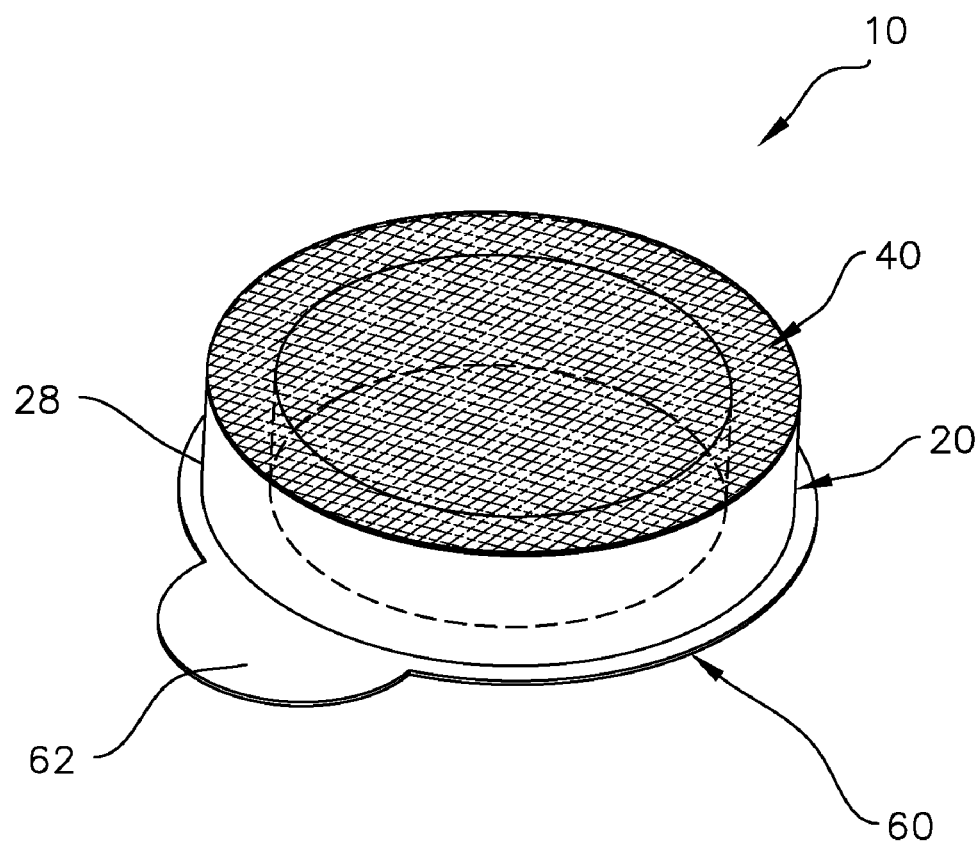
FIG. 1 represents an isometric view of the instant invention.

Referring now to the drawings, the apparatus to protect a piercing is generally referred to with numeral 10.

Figure 2:
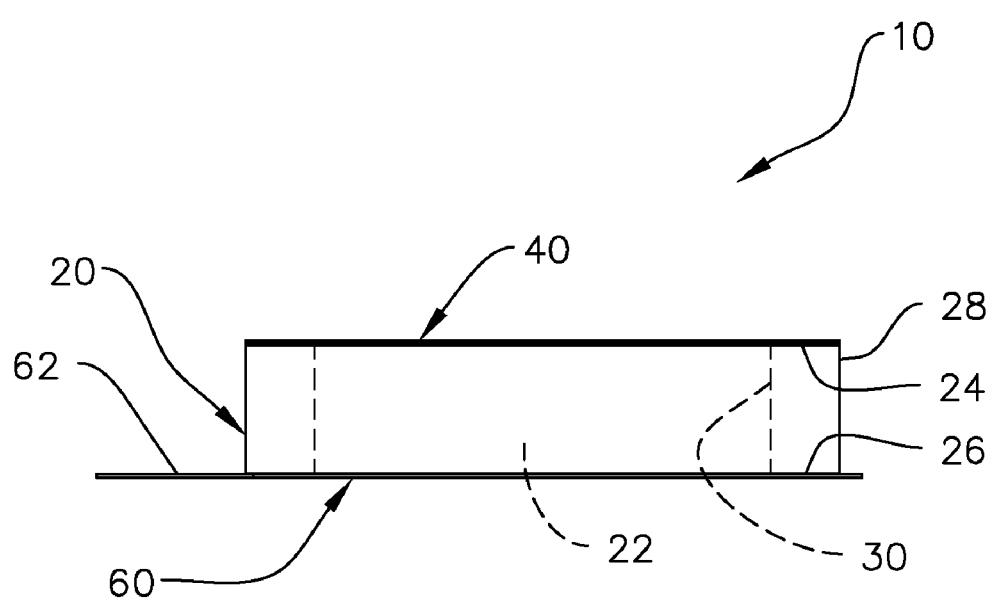
FIG. 2 shows a front elevational view of the instant invention.

As seen in FIGS. 1 and 2, instant invention 10 includes body assembly 20, permeable cover 40, and removable cover 60. In the preferred embodiment, body assembly 20 is made of a soft resilient material. Such a material can be, but is not limited to foam, sponge, or other material having similar characteristics. Body assembly 20 comprises top face 24 that is opposite to bottom face 26, and exterior wall 28 and interior wall 30 that define cavity 22. It is noted that cavity 22 extends inwardly from said interior wall 30. In the illustrated embodiment, top face 24 is parallel to bottom face 26, and exterior wall 28 is an exact shape to that of interior wall 30.

Permeable cover 40 is made out of a permeable material and has a cooperative shape and dimension to cover top face 24 and cavity 22 of body assembly 20. Permeable cover 40 is fixedly secured to top face 24, whereby top face 24 has adhesive means to keep permeable cover 40 fixedly secured thereon. Permeable cover 40 covers cavity 22, whereby ambient air can enter and/or circulate therethrough to allow healing of a body and facial piercing such as piercing P, seen in FIGS. 3 and 4, and specifically the opening created by the piercing P, and surrounding area of the piercing P.

Removable cover 60 has a cooperative shape and dimension to cover bottom face 26 and cavity 22. It is noted that bottom face 26 has an adhesive film that serves as adhesive means, and that removable cover 60 is removably attached to bottom face 26. Removable cover 60 protects bottom face 26 when instant invention 10 is not in use and furthermore, prevents foreign matter from accumulating within cavity 22. Removable cover 60 has tab member 62 to facilitate the removal of removable cover 60 from bottom face 26 when instant invention 10 is to be used.

Figure 3:
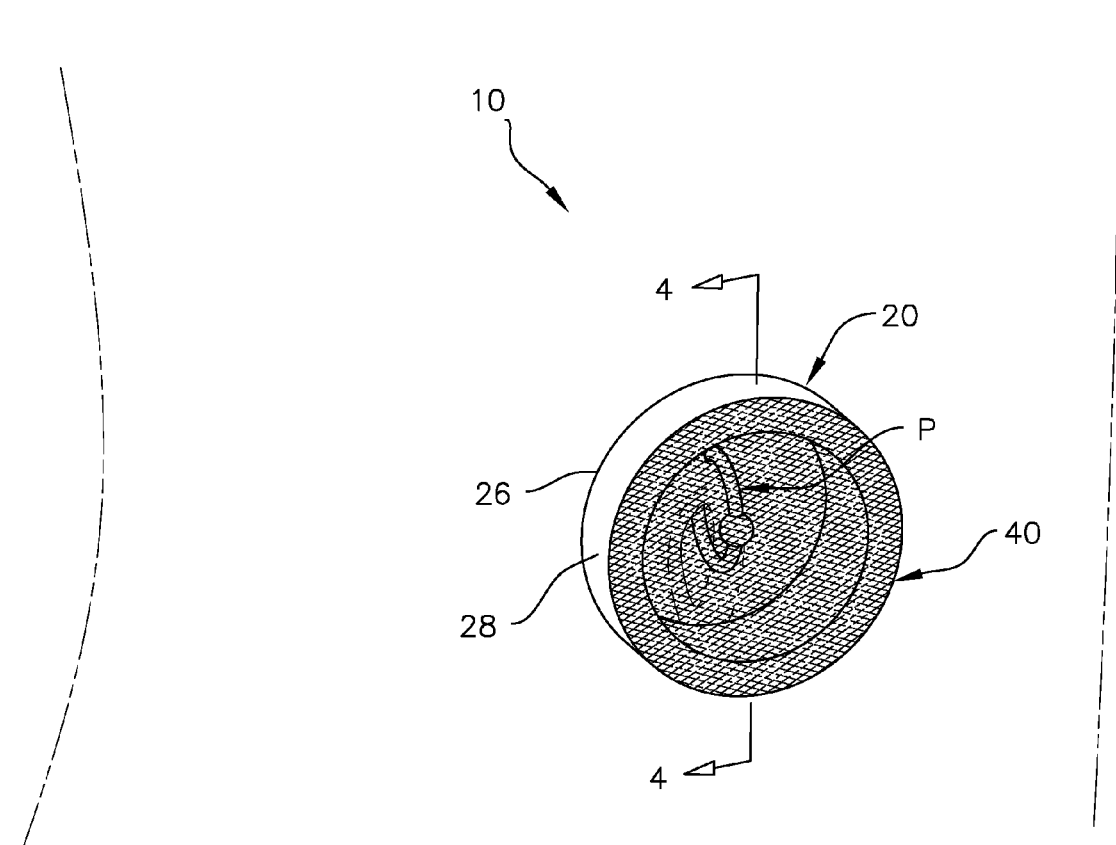
FIG. 3 is an isometric view of the instant invention as worn by a person, showing the disposition of the piercing within the cavity of the body assembly.
Figure 4:
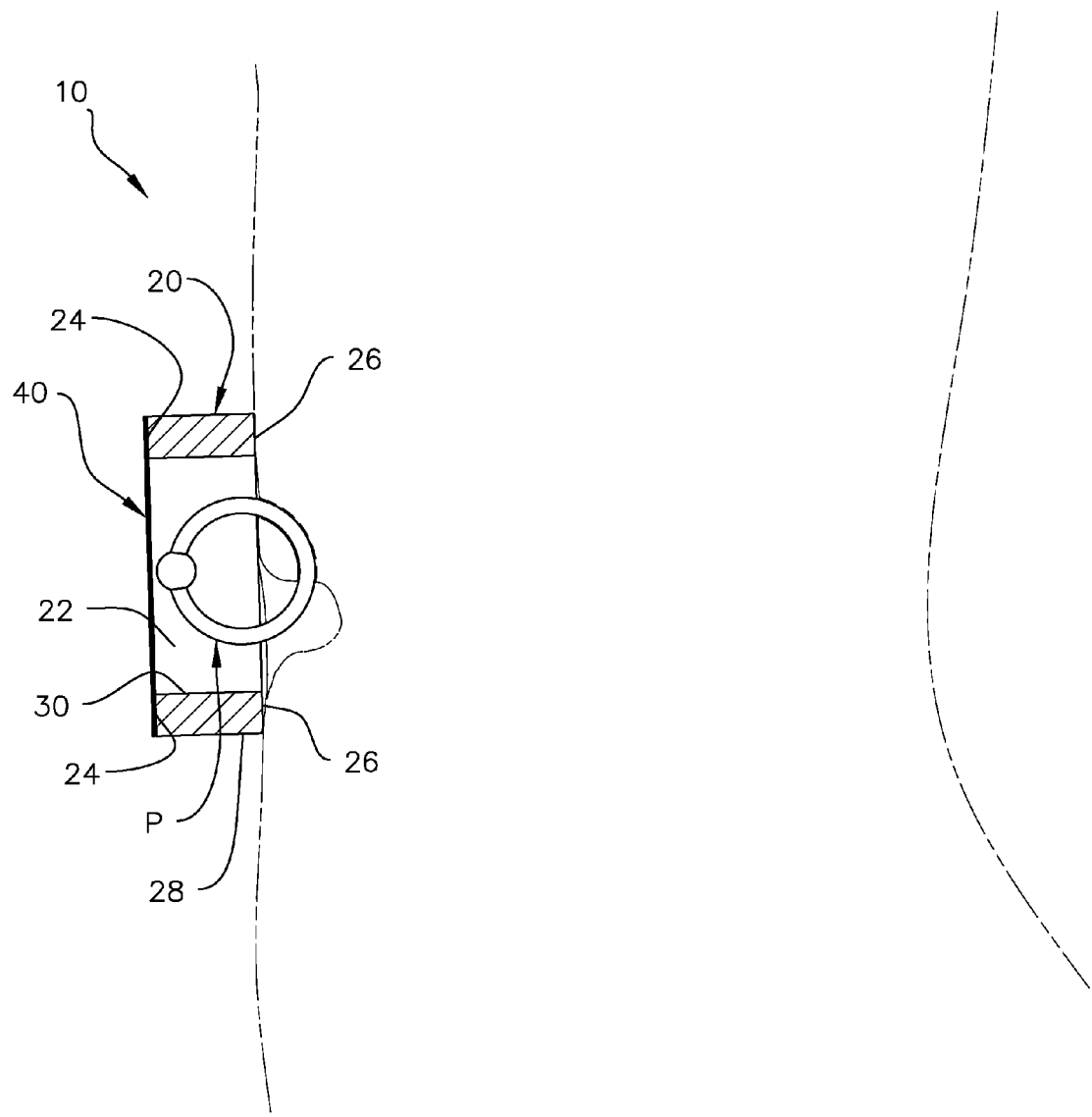
FIG. 4 is a cross-section view taken along line 4-4 as seen in FIG. 3.

As seen in FIGS. 3 and 4, in operation, a person removes removable cover 60 from bottom face 26 via tab member 62. The person then places bottom face 26 around piercing P so that piercing P is housed within cavity 22, whereby the adhesive film on bottom face 26 allows bottom face 26 to adhere to the area around piercing P.

In alternate embodiments of present invention 10, body assembly 20 and/or cavity 22 may be of a variety of shapes, including but are not limited to: circular, oval, square, pentagonal, and hexagonal. Accordingly, permeable cover 40 and removable cover 60 should have cooperative shapes and dimensions to complement the shape of body assembly 20 for the purposes defined above.

During body and facial piercing aftercare, instant invention 10 protects piercing P and its affected area during a healing period that can last days, weeks, months, or longer by protecting piercing P from bacterial and viral infections that can develop from dirt, sand, or other irritating/infecting substances. Once worn by a person, instant invention 10 prevents piercing P from coming into contact with unwanted objects and/or substances, such as when sleeping on one's stomach or face down. Furthermore, instant invention 10 helps prevent and/or reduce trauma, usually associated with unintended entanglement of the piercing jewelry with another object.

In the case of a belly-button ring, such as the one illustrated in FIGS. 3 and 4, the person can wear clothes, and specifically a pant, skirt, short, or other article of clothing that covers piercing P over instant invention 10.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An apparatus to protect a piercing, comprising:
   A) a body assembly comprising top and bottom faces, an exterior wall, and an interior wall, said body assembly further defining a cavity extending inwardly from said interior wall, said body assembly being of a uniform and symmetrical tubular shape with no flange extending therefrom and said body assembly being of a predetermined height, said top and bottom faces being flat surfaces, and said exterior wall being of an exact shape to that of said interior wall, said top and bottom faces being connected by said exterior wall to define said predetermined height and having no additional material extending therefrom, said body assembly is made out of a soft resilient material;
   B) a permeable cover having a first cooperative shape and dimension to cover said top face and said cavity, said permeable cover is fixedly secured to said top face and extends to an exterior edge of said top face, whereby said top face has a first adhesive to keep said permeable cover fixedly secured thereon, said permeable cover covers said cavity to allow ambient air to enter and circulate therethrough to allow healing of a body or facial piercing, and specifically an opening created by said body or facial piercing, and surrounding area around said body or facial piercing; and
   C) a removable cover having a second cooperative shape and dimension to cover said bottom face and said cavity, said bottom face has a second adhesive, and said removable cover is removably attached to said bottom face, said removable cover prevents foreign matter from accumulating within said cavity while said removable cover remains attached to said bottom face, said removable cover extending outward beyond the periphery of said exterior wall and having a tab member to facilitate removal of said removable cover from said bottom face.

2. The apparatus to protect a piercing set forth in claim 1, further characterized in that said cavity is of a third cooperative shape and dimension to house said body or facial piercing.

3. The apparatus to protect a piercing set forth in claim 2, further characterized in that said body assembly is circular, oval, square, pentagonal, or hexagonal in shape.

4. The apparatus to protect a piercing set forth in claim 3, further characterized in that said top face is parallel to said bottom face.

5. An apparatus to protect a piercing, consisting of:
   A) a body assembly comprising top and bottom faces, an exterior wall, and an interior wall, said body assembly further defining a cavity extending inwardly from said interior wall, said body assembly being of a uniform and symmetrical tubular shape with no flange extending therefrom and said body assembly being of a predetermined height, said top and bottom faces being flat surfaces parallel to each other, and said exterior wall being of an exact shape to that of said interior wall, said top and bottom faces being connected by said exterior wall to define said predetermined height and having no additional material extending therefrom, said body assembly is made out of foam or sponge;
   B) a permeable cover having a first cooperative shape and dimension to cover said top face and said cavity, said permeable cover is fixedly secured to said top face and extends to an exterior edge of said top face, whereby said top face has a first adhesive to keep said permeable cover fixedly secured thereon, said permeable cover covers said cavity to allow ambient air to enter and circulate therethrough to allow healing of a body or facial piercing, and specifically an opening created by said body or facial piercing, and surrounding area around said body or facial piercing; and
   C) a removable cover having a second cooperative shape and dimension to cover said bottom face and said cavity, said bottom face has a second adhesive, and said removable cover is removably attached to said bottom face, said removable cover prevents foreign matter from accumulating within said cavity while said removable cover remains attached to said bottom face, said removable cover extending outward beyond the periphery of said exterior wall and having a tab member to facilitate removal of said removable cover from said bottom face.

6. The apparatus to protect a piercing set forth in claim 5, further characterized in that said cavity is of a third cooperative shape and dimension to house said body or facial piercing.

7. The apparatus to protect a piercing set forth in claim 6, further characterized in that said body assembly is circular, oval, square, pentagonal, or hexagonal in shape.

8. An apparatus to protect a piercing, comprising:
   A) a body assembly comprising top and bottom faces, an exterior wall, and an interior wall, said body assembly further defining a cavity extending inwardly from said interior wall, said body assembly being of a uniform and symmetrical tubular shape with no flange extending therefrom and said body assembly being of a predetermined height, said top and bottom faces being flat surfaces parallel to each other, and said exterior wall being of an exact shape to that of said interior wall, said top and bottom faces being connected by said exterior wall to define said predetermined height and having no additional material extending therefrom;
   B) a permeable cover having a first cooperative shape and dimension to cover said top face and said cavity, said permeable cover is fixedly secured to said top face, whereby said top face has a first adhesive to keep said permeable cover fixedly secured thereon, said permeable cover covers said cavity to allow ambient air to enter and circulate therethrough to allow healing of a body or facial piercing, and specifically an opening created by said body or facial piercing, and surrounding area around said body or facial piercing; and C) a removable cover having a second cooperative shape and dimension to cover said bottom face and said cavity, said bottom face has a second adhesive, and said removable cover is removably attached to said bottom face, said removable cover prevents foreign matter from accumulating within said cavity while said removable cover remains attached to said bottom face, said removable cover extending outward beyond the periphery of said exterior wall and having a tab member to facilitate removal of said removable cover from said bottom face.

9. The apparatus to protect a piercing set forth in claim 8, further characterized in that said body assembly is made out of a soft resilient material.

10. The apparatus to protect a piercing set forth in claim 8, further characterized in that said cavity is of a third cooperative shape and dimension to house said body or facial piercing.

\* \* \* \* \*